United States Patent [19]

Bulich

[11] 3,963,575

[45] June 15, 1976

[54] PRODUCING PULLULANASE WITH ORGANISMS HAVING A SUPERIOR CAPACITY TO ELABORATE PULLULANASE

[75] Inventor: Anthony A. Bulich, Decatur, Ill.

[73] Assignee: A. E. Staley Manufacturing Company, Decatur, Ill.

[22] Filed: Feb. 25, 1974

[21] Appl. No.: 445,190

[52] U.S. Cl. ............................. 195/31 R; 195/62; 195/65; 195/66 R; 195/112; 195/114
[51] Int. Cl.².................. C12D 13/02; C12D 13/10; C07G 7/02
[58] Field of Search ................. 195/65, 66 R, 31 R, 195/62, 114, 112

[56] References Cited
UNITED STATES PATENTS

| | | | |
|---|---|---|---|
| 3,654,088 | 4/1972 | Coker et al. | 195/31 R |
| 3,766,014 | 10/1973 | Masuda et al. | 195/65 |
| 3,806,419 | 4/1974 | Heady | 195/66 R |
| 3,827,940 | 8/1974 | Sugimoto et al. | 195/66 R |

*Primary Examiner*—A. Louis Monacell
*Assistant Examiner*—Thomas G. Wiseman
*Attorney, Agent, or Firm*—M. Paul Hendrickson; Charles J. Meyerson

[57] ABSTRACT

Improved pullulanase yields are achieved by incubating culture mediums containing pullulanase producing mutants of the Klebsiella genus. The mutants generally produce approximately equivalent amounts of extracellular and superficially bound pullulanase in an easily recoverable and usable form. Optimum pullulanase production is achieved when amylopectin is used as the sole carbohydrate source. Conventional pullulanase inducers such as maltose, maltotriose and/or pullulan repress the mutant strains capacity to produce pullulanase. The mutants are capable of elaborating pullulanase in a culture media containing dextrose as the sole carbohydrate source.

32 Claims, No Drawings

PRODUCING PULLULANASE WITH ORGANISMS HAVING A SUPERIOR CAPACITY TO ELABORATE PULLULANASE

BACKGROUND OF THE INVENTION

Within recent years, the art has recognized the potential commercial significance of enzymes possessing specificity in hydrolyzing alpha-1,6-glucosidic starch linkages. Conventional amylases are not completely effective in hydrolyzing 1,6 starch linkages and frequently form undesirable starch hydrolyzate by-products. By employing alpha-1,6-glucosidic hydrolyzing enzymes (e.g., pullulanase) in conjunction with other amylases, the conversion syrup industry would be able to produce a broader spectrum of starch hydrolyzates and conversion syrup products. If pullulanase were available at an economically feasible cost, starch conversion syrups of a superior quality could be produced at a significantly lower price.

In general, pullulanase is produced by inoculating and fermenting a culture media containing assimilable carbon, nitrogen and mineral nutrients with *Aerobacter aerogenes* under conditions conductive to its growth. In some processes, pullulanase production by the *Aerobacter aerogenes* is permitted to occur simultaneously with cell propagation. In other processes, pullulanase elaboration does not occur until late in growth phase. In some processes, pullulanase production is intentionally repressed by employing a culture media deficient in saccharide materials which are deemed essential for pullulanase synthesis. Upon achieving sufficient *Aerobacter aerogenes* growth, the cells are then induced to produce pullulanase with a carbohydrate such as maltose, maltotriose or pullulan.

As a class, the *Aerobacter aerogenes* strains heretofore employed in the pullulanase production stage generally possesses a characteristic of producing divergent levels of extracellular enzyme, tightly bound enzyme and superficially bound enzyme when different carbohydrate source materials are employed. The ratio of extracellular to cell bound enzyme produced by an *Aerobacter aerogenes* organism is often reversed simply by altering or substituting one carbohydrate for another in the fermentation process. Depending upon the particular carbohydrate source, the fermentation process will normally favor either extracellular pullulanase production (e.g., more than 75%) or cell bound pullulanase production (e.g., about 75% or more).

As a class, *Aerobacter aerogenes* organisms are incapable of elaborating pullulanase when dextrose is employed as a sole carbohydrate source. However, if the propagation and pullulanase production is conducted simultaneously in the presence of an excess amount of a carbohydrate inducer, extracellular pullulanase is primarily elaborated (e.g., about 75–80%) with the remaining portion being tightly bound on the organisms. When equivalent weights of dextrose (for growth) and carbohydrate inducer (e.g., maltose) are employed for cell propagation and enzyme production, extracellular pullulanase production will usually decrease (e.g., about 20%) while superficially cell bound pullulanase increases to a level of about 70% with the remaining portion of the total enzyme being in a tightly bound form. By conducting the *Aerobacter aerogenes* pullulanase process via a cell propagation and subsequent pullulanase production by addition of inducers thereto, the *Aerobacter aerogenes* will primarily produce cell bound enzymes at a level of about 75% with the balance being extracellular enzyme.

In Biochemische Zietschrift 334, 79–95 (1961) H. Bender and K. Wallenfels reported that *Aerobacter aerogenes* belonging to the Enterobactericeae family, produced pullulanase. Inducers such as maltose, maltotriose or pullulan were reported as being an essential carbohydrate for pullulanase production. Pursuant to this process, about 75–80% of the total pullulanase elaborated by the organisms is extracellular. Due to the difficulties in purifying and recovering the pullulanase, Wallenfels et al.[1] subsequently proposed propagating the organism in the presence of equal amounts of glucose and maltose. By this method extracellular pullulanase was reportedly decreased to a level of about 20% or less, with the remaining pullulanase being localized near the organisms surface. This localized pullulanase was disclosed as being easily liberated by surfactants.

[1] — Biochemical & Biophysical Research Communications, Vol. 22, No. 3, 1966 — pp. 254–261.

In U.S. Pat. Nos. 3,654,087, 3,654,088 and 3,654,089 (by Coker et al.) it is disclosed that improved pullulanase yields are achieved when *Aerobacter aerogenes* pullulanase production is conducted in a two-stage process. In the first stage of the Coker et al. process, *Aerobacter aerogenes* growth is favored without appreciable pullulanase production. This is generally accomplished by conducting the fermentation in the presence of carbohydrates such as dextrose as a sole or principle carbohydrate. Upon achieving a high level of cell propagation, the *Aerobacter aerogenes* are then induced to produce pullulanase with carbohydrate inducers. In U.S. Pat. No. 3,654,088, it is reported that improved pullulanase yields are achieved in the production stage when induced cells are incubated in the presence of amylopectin. In general, the pullulanase produced by the *Aerobacter aerogenes* in the aforementioned Coker et al. patents is primarily cell bound enzyme (e.g., about 65–75% or more).

Numerous patents have reported different microbial strains as being capable of producing α-D-1,6-glucosidic hydrolyzing enzymes (e.g., see U.S. Pat. Nos. 3,560,345 by Yokobayashi et al. *Pseudomonas amyloderamosa*, 3,716,455 by Ueda et al. *Escherichia intermedia* and British Pat. No. 1,260,418.

Pullulanase production with culture mediums containing starch hydrolyzates have also been reported. In U.S. Pat. No. 3,560,345 by Yokobayashi et al., any carbohydrate material having α-1,4 or 1,6-glucosidic linkages are reported as a suitable carbon source for the synthesis of extracellular isoamylases. According to the Yokobayashi et al. patentees, extracellular yields of about 180–220 units/ml.[2] are reported via incubation in culture mediums containing maltose or soluble starch as a sole carbohydrate source. Table 5 of the Yokobayashi et al. patent indicates that pullulanase yields from the incubation of a culture media comprised of maltose, ammonium salts and soybean hydrolyzates (up to 130 units/ml) are greater than those wherein starch hydrolyzates are employed as a carbohydrate source material. U.S. Pat. No. 3,622,460 by Masuda et al., discloses maximum yields of about 125 alpha-1,6-glucosidase units/ml.[2] via employing a production culture medium which contains starch hydrolyzates (D.E. of 2–15%) in combination with soybean hydrolyzates as a nitrogen source material. In Canadian Pat. No. 901,503 by Heady, starch hydrolyzates having a D.E. of 5–40 are used to facilitate pullulanase production.

2 — Units are determined by an iodine assay which comparatively gives higher unit values than the assay method used to define the units herein.

The art has sought a process which would provide high pullulanase yields in a readily recoverable and usable form. Some processes produce relatively high pullulanase yields in a form unsuitable for recovery. Other processes produce a readily recoverable pullulanase in low yields.

Although there is a commercial need for pullulanase at a price which would economically justify its usage in starch conversion processes, pullulanase can neither be obtained at a price nor in a quantity as necessitated by the starch syrup industry. Notwithstanding this need, the art has been unable to discover and develop an organism capable of producing high pullulanase yields under process conditions wherein the pullulanase is readily and economically recoverable in a form suitable for commercial usage.

OBJECTS

It is an object of the invention to increase pullulanase yields.

Another object of the invention is to obtain high pullulanase yields in a relatively short period of time.

A still further object is to provide a process wherein microbially produced pullulanase can be easily and economically recovered from a production culture medium.

An additional object of the invention is to utilize pullulanase producing mutants which have superior pullulanase elaboration properties.

It is also an object of the present invention to provide a production culture medium which in combination with pullulanase producing mutants will elaborate significantly improved pullulanase yields.

DESCRIPTION OF THE INVENTION

In the present invention there is provided a method for producing pullulanase by inoculating an aqueous nutrient medium containing assimilable carbon and assimilable nitrogen sources with an aerobic, pullulanase producing microbial organism to provide a culture thereof, incubating the culture under conditions conducive to the production of pullulanase and thereafter recovering a pullulanase preparation having a greater potency than the incubated culture, the improvement which comprises:

A. inoculating a nutrient medium with a pullulanase producing microbial mutant, said nutrient medium containing amylopectin (on a weight basis) as the major carbon source and having a dry solids weight ratio of amylopectin to a carbohydrate source member selected from the group consisting of maltose, dextrose, lactose and pullulan of no less than 4:1, said pullulanase producing mutant being characterized as:
  a. elaborating at least three times more pullulanase when amylopectin of a D.E. of less than 2.0 is employed as the sole carbohydrate source comparative to pullulanase elaboration in a nutrient medium wherein the major carbohydrate (on an equivalent weight basis) is a carbohydrate source member;
  b. elaborating pullulanase at a ratio of extracellular pullulanase to superficially bound cell pullulanase between about 2:3 to less than about 7:3 when said mutant is elaborated in a nutrient medium containing amylopectin as the sole carbohydrate source; and
  c. elaborating pullulanase in a nutrient medium which contains dextrose as a sole carbohydrate source;
B. incubating the pullulanase producing mutant in a nutrient medium for a period of time sufficient to provide a culture which contains at least 350 units of pullulanase for each milliliter of nutrient medium and a ratio of extracellular pullulanase to superficially bound pullulanase is between about 2:3 and less than about 7:3.

Comparative to the pullulanase producing organisms of the type initially disclosed by Wallenfels et al.[3], the present organisms possess atypical metabolic characteristics. These metabolic differences are illustrated by the substitution of divergent carbohydrate source materials in an aqueous nutrient media consisting of (on a dry solids basis) 2% Bacto-peptone, 0.5% ammonium acetate, 0.05% sodium citrate, 0.10% potassium (monohydrogen) orthophosphate ($K_2HPO_4$), 0.1% potassium (dihydrogen) orthophosphate ($KH_2PO_4$), 0.05% magnesium sulfate (epsom salt), 0.05% potassium chloride, 0.001% ferrous sulfate (Melanterite) and water.

3 — The term *Aerobacter aerogenes* has been consistently applied by the art in identifying the pullulanase producing organism of Wallenfels et al. type (possibly because of their original characterization thereof as "behaving as Aerobacter") notwithstanding more recent classifications which indicate the organism is of the Klebsiella genus (Klebsiella Pneumonia).

In general, cell propagation by the present mutants is approximately equivalent for carbohydrate source materials such as pullulan, lactose, dextrose, maltose, corn starch hydrolyzates of a 5–25 D.E., gelatinized starch and gelatinized amylopectin. However, the amount of pullulanase produced by the mutants is definitely affected by the specific carbohydrate source material in the culture media. Dextrose, as a sole carbohydrate nutrient suppresses the mutants elaboration of extracellular enzyme (e.g., about 30%). Other carbohydrates such as lactose, maltose, maltotriose, pullulan, yellow dent corn starch hydrolyzates, assimilable high amylose starches, as a sole carbohydrate nutrient source effectuate elaboration of approximately equivalent amounts of extracellular to superficially bound pullulanase (on a unit basis).

When dextrose is employed as a sole saccharide source, *Aerobacter aerogenes* ATCC 15050 fails to elaborate pullulanase. In contrast, the present mutants have the capacity to produce a small amount of extracellular enzyme in a culture medium which contains dextrose as the sole carbohydrate source (about 10 pullulanase units/ml. or more of which approximately 30% is extracellular pullulanase). In the above mentioned aqueous nutrient medium with lactose as the exclusive carbohydrate source, the mutants herein elaborate above 8 times more pullulanase than will *Aerobacter aerogenes* ATCC 15050. Carbohydrate inducers such as maltose, maltotriose and pullulan (disclosed by many as being essential for *Aerobacter aerogenes* pullulanase production), repress the mutants' pullulanase production and elaboration capacity.

Although the mutants are capable of producing pullulanase in the presence of fermentable starch hydrolyzates, the higher molecular weight, branched starch fractions (e.g., amylopectin) facilitate pullulanase elaboration and yields. As illustrated in Table I of Example II, gelatinized substantially unhydrolyzed amylopectin (as a sole carbohydrate source) optimizes pullulanase production by the mutants. Comparatively, a gelatinized corn starch further decreases pullulanase production yields while starch hydrolyzates thereof (e.g., a 12 D.E. corn starch) further inhibit the mutants pullulanase production capacity. Fermentable sugars (during the pullulanase production stage), have a repressive effect upon the mutants capacity to produce pullulanase.

Another salient characteristic of the mutants is the proportion of extracellular pullulanase to loosely bound elaborated by the mutant. When amylopectin is utilized in the aforementioned base culture, *Aerobacter aerogenes* elaborates a relatively low amount of extracellular enzyme and a high proportion of cell bound pullulanase. Conversely, incubation of the pullulanase mutants with amylopectin generally results in production of a pullulanase unit ratio of extracellular to loosely bound pullulanase of greater than 2:3 to less than 7:3 (usually less than 2:1) with a substantially lesser amount of pullulanase tightly cell-bound (e.g., less than 20% of total pullulanase elaboration is in the cell bound form). Due to the high proportion of pullulanase elaboration in extracellular and superficially bound form, the processing ease and cost encountered in recovering high pullulanase yields in a commercially usable form are a particular advantage of practicing the present process. By practicing the present process, the amount of intracellular or internally bound pullulanase (which normally requires cellular disintegration for recovery) can be minimized to less than about 10% (preferably less than about 5%) of the total pullulanase production. During the enzyme production stage, a high proportion of pullulanase is elaborated by the mutant into the aqueous culture media phase as a water-soluble enzyme. In a more limited aspect of the present invention, the mutants herein are characterized as elaborating a unit ratio of extracellular pullulanase to superficially bound enzyme between about 3:4 to about 2:1 (preferably about 1:1 to about 3:2) when a carbohydrate source material (at 2% dry solids level) selected from the group consisting of gelatinized amylopectin, gelatinized corn starch, maltose, lactose, pullulan and maltodextrin is used as a sole carbohydrate source in the aforementioned aqueous nutrient culture medium.

When the mutants herein are incubated with the aforementioned aqueous nutrient medium they are further characterized as being substantially free from mucilaginous polysaccharide materials. Excessive, cell-produced, mucilaginous polysaccharide will adversely affect the yields of recoverable pullulanase. In the production and recovery stages, the absence of this mucilaginous material facilitates the transfer and dispersion of pullulanase into the aqueous phase of the production culture media. Upon completion of the pullulanase production stage, the superficially bound pullulanase is not imbibed or occluded by cell produced mucilaginous material. By the addition of detergents, the superficially bound cell bound pullulanase can be easily converted to a soluble form and liberated therefrom.

The organism employed in this invention possesses the capacity of yielding (on a commercial production basis) greater than 350 units of pullulanase for each milliliter of production broth. A particular processing advantage indigenous to these organisms is the characteristics of the pullulanase which the organisms produce. The organisms capacity to produce pullulanase substantially in the extracellular and superficially bound form makes it easy to recover at least 80% of the total pullulanase in the final production broth. In a production culture media consisting essentially of amylopectin as a carbohydrate source, pullulanase yields of superficially bound and extracellular pullulanase of at least 500 units/ml. can easily be prepared herein. Advantageously, the process of the present invention is conducted with a nutrient culture media under incubation conditions such that the pullulanase yields are greater than 750 units per ml. of culture media and more than 85% (e.g., between 85% to about 95% or more) of the total pullulanase produced thereby is of the extracellular and superficially bound form. In the preferred embodiments of the invention, greater than 90% of the total pullulanase production is in these two forms.

The mutants capacity to produce pullulanase is significantly enhanced in the presence of a production culture media which contains amylopectin as a major carbohydrate source material (on a dry solids weight basis). A production culture medium containing amylose as a major carbohydrate (weight basis) will not totally suppress pullulanase production but the pullulanase yields are significantly lower in comparison to those of a higher amylopectin content.

A variety of starches may be utilized as an amylopectin source. Exemplary starches include those having a relatively high amylopectin content (e.g., more than 70%). These starches typically have a gelatinization temperature of less than about 80°C. Illustrative amylopectin containing starches include tubers and root starches (e.g., potato, tapioca, canna, arrowroot, sweet potato, etc.), the cereal starches (e.g., corn, sorghum, wheat, rice, waxy maize, waxy rice, waxy sorghum, etc. mixtures thereof and the like. Starches consisting essentially of amylopectin (e.g., those having an amylose content of less than 10% and more than 90% amylopectin) such as waxy maize, waxy corn, waxy sorghum, waxy rice, waxy barley, mixtures thereof and the like, are particularly effective carbohydrates for optimizing pullulanase production.

As in conventional pullulanase processes, assimilable carbohydrates are utilized in the production culture medium. Gelatinized starch and/or partially hydrolyzed (e.g., acid or enzyme thinned starches) in an amount sufficient to enable the mutants to metabolize the starch source with concomitant pullulanase production can be used as an assimilable carbohydrate source. Starch hydrolyzates having an appreciable amount of fermentable sugars will repress pullulanase production by the mutants. On a comparative basis, pullulanase production decreases as the D.E. of a starch hydrolyzate increases. Starch hydrolyzates of a D.E. greater than 30% will significantly repress pullulanase production comparative to those at a D.E. of less than 20%. Likewise a starch hydrolyzate having a D.E. of less than 10% will enable the mutants to produce a greater amount of pullulanase than those of a higher D.E. Improved pullulanase yields are achieved with either unthinned amylopectin or partial starch hydrolyzates which have a D.E. less than 5.0%. Optimum pullulanase yields are effectuated by incubating the mutants in the presence of pasted amylopectin substrates having a D.E. of less than about 2.0%.

The production culture medium should contain a sufficient amount of carbohydrate source material to enable the mutants to further propagate and produce pullulanase therein. In general, the pullulanase production is conducted in the presence of amylopectin in an amount sufficient to produce the pullulanase yields mentioned above. Broadly, the amount of carbohydrate material may range from about 1 to about 10 parts by weight carbohydrate for each 100 parts by weight of water in the production culture medium. Amylopectin in an amount of at least about 1 to about 6 parts by weight enhances both the rate and amount of pullulanase produced by the mutants. Advantageously, the production culture medium has a weight ratio of amylopectin to non-amylopectin carbohydrate source material of at least 7:3 and preferably greater than 9:1. A production culture medium essentially free from other carbohydrates and containing from about 2 to about 4 parts by weight amylopectin for each 100 parts by weight water provides exceptionally high pullulanase yields.

In producing pullulanase it is conventional to utilize a seed culture or an inoculum to provide viable organisms for the pullulanase production culture medium. In commercial practice, the seed culture will contain a high cell population which is used to inoculate the production culture medium. Depending upon the particular process employed in providing the seed culture, pullulanase may be suppressed or favored in development of this seed culture. In the present invention, the seed culture may be cultivated with a broad range of carbohydrates which are conducive to propagation of the organism irrespective of whether the carbohydrate inhibits or favors pullulanase production.

The production culture medium may be inoculated with viable mutants by conventional seed culture techniques. The seed culture medium per se or propagated mutants, may be utilized to inoculate the production culture medium. Because most carbohydrates tend to suppress pullulanase production, it is advantageous to also use amylopectin in preparing the seed culture medium. By employing amylopectin as a carbohydrate source for the seed culture, it may be used directly as an inoculum without adversely affecting over-all carbohydrate balance of the pullulanase production culture medium.

In order to effectively produce pullulanase an assimilable nitrogen source material in an amount sufficient to enable the mutants to produce pullulanase should be provided as an essential nutrient in the production culture medium. The nitrogen source material may be provided in the production culture medium prior to its inoculation or may be incrementally added throughout the propagation and pullulanase production cycle. During the initial production stages, the nitrogen source is primarily metabolized by the mutants for cell growth. During the later incubation stages, the nitrogen source is primarily utilized by the mutants for pullulanase production. The amount of nitrogen source material can vary considerably, but will usually range from between about 2 to about 15 parts by weight dry solids for each 100 parts by weight of production culture medium water.

Organic nitrogen containing compositions may be used as an assimilable nitrogen source material in the present process. Typical organic nitrogen sources of a water soluble type include urea, peptone, meat, yeast extracts, corn steep liquor, casein hydrolyzates, fish meal, vegetable hydrolyzates (e.g., soybeans, cotton seeds, peanuts) and cereal proteinaceous material (e.g., wheat, bran, rice, corn protein, etc.), amino acids (e.g., glycine, glutamic acid, aspartic acid, alanine, etc.) mixtures thereof and the like.

In a preferred embodiment of the invention, corn steep liquor is utilized as an assimilable, organic nitrogen source. If corn steep liquor is used as the sole organic nitrogen source, pullulanase production will be inhibited by either an excessive or insufficient amount of corn steep liquor. For example, a production culture medium which contains more than 6 parts by weight corn steep liquor (dry solids basis) will tend to suppress pullulanase elaboration. When less than about 2 parts by weight corn steep liquor (dry solids basis) is exclusively utilized as an assimilable organic nitrogen source, the culture media generally contains sufficient nitrogen to sustain cell growth but pullulanase production becomes significantly impaired thereby. When it is desired to employ corn steep liquor as the exclusive nitrogen source, high pullulanase yields will normally be achieved when the corn steep liquor dry solids is between about 2 to about 5 parts by weight for each 100 parts by weight of production culture medium water. At about 4 parts by weight corn steep liquor dry solids level, optimum pullulanase production results are achieved.

The combination of an assimilable inorganic nitrogen source and an assimilable organic nitrogen source in the production culture medium has been found to further increase over-all pullulanase production by the mutants. Conventional, water-soluble nitrogen sources may be utilized as an inorganic nitrogen supplement. Ammonia, ammonium salts (e.g., ammonium chloride, ammonium nitrate, ammonium carbonate, ammonium acetate, ammonium sulfates) ammonium phosphate, the alkali nitrates (e.g., sodium nitrate), mixtures thereof and other similar water soluble salts are illustrative supplemental, inorganic nitrogen source materials.

The predominant nitrogen source material (on a weight basis) in the production culture media will normally be the organic nitrogen source materials. Weight ratios of organic nitrogen source materials to inorganic typically range from less than about 1:1 up to about 15:1 or higher. Improved pullulanase yields are achieved at an organic to inorganic nitrogen weight ratio between about 3:1 to less than 10:1 (preferably between about 4:1 to about 6:1).

In general, the amount of water soluble nitrogen salts can range from about 0.25 parts to about 2 parts by weight for each 100 parts by weight water of production culture medium. The assimilable ammonium salts are particularly suitable as an inorganic nitrogen source material. Ammonium acetate and ammonium sulfate are preferred inorganic nitrogen sources for optimizing pullulanase yields. The total amount of pullulanase produced by the mutants remains relatively constant above a 1% by weight inorganic nitrogen source level. About 0.5 parts to about 1 part by weight of the water soluble nitrogen containing salts (preferably at about 0.75 parts) is particularly effective in enhancing both the pullulanase rate and yields.

Pullulanase elaboration by the mutants is also significantly increased when the production culture medium contains a small amount of an assimilable iron. Similar to all organisms, the mutants herein require trace amounts of iron for growth. Such trace amounts of iron, as conventionally employed in culture mediums to sustain cell propagation, are generally insufficient for effective elaboration of pullulanase by the mutants. By supplementing the production culture medium with a small amount of excess assimilable iron (i.e., an amount more than required for cell propagation), pullulanase production is significantly enhanced. In the absence of supplemental iron, an incubated culture medium will usually elaborate pullulanase. In order to optimize pullulanase production it is important, at least during the pullulanase production stage of the process, to enrich the production culture medium with an effective amount of an assimilable iron sufficient to have a measurable effect upon the pullulanase elaboration.

The amount of supplemental iron necessary to achieve maximum pullulanase elaboration for mutants from the Klebsiella genus is partially dependent upon the particular mutant strain which is utilized in the process. Klebsiella pneumoniae NRRL B-5783 does not effectively produce pullulanase in the absence of supplemental iron. Although *Klebsiella pneumoniae* NRRL B-5780 and *Klebsiella pneumoniae* NRRL B-5784 will elaborate a substantial amount of pullulanase in the absence of supplemental iron, these yields are significantly below their optimum. The effect of assimilable iron upon the production capacity of these mutants is further illustrated by the Examples.

Production culture medium containing ferrous ions (e.g., ferrous sulfate) as a sole iron source also usually provide improved pullulanase yields from those which only contain ferric ion (e.g., ferric chloride). A substantial reduction in ferrous ion or an insufficient amount thereof can result in a decrease of pullulanase yields. The assimilable iron pullulanase requirements of the mutants may be derived from a variety of conventional sources. Illustrative ferrous compounds include the ferrous salts of acetate, carbonate, citrate, lactate, nitrate, sulfate, sulfite, thiosulfate, mixtures thereof and the like. Other materials which indigenously contain trace amounts of iron ions such as corn steep liquor and tap water rich in ferrous or ferric compounds may also be used as an iron source. A production culture medium containing more than 1.0 mg. and advantageously more than 2.0 mg. of ferrous ion for each liter of production culture medium (e.g., preferably between about 3.0 mg. to about 5.0 mg.) will provide further improvements in total pullulanase production. Corn steep liquor normally contains trace amounts of iron. For optimum pullulanase production, additional ferrous compounds are added to a culture media containing the corn steep liquor to provide the appropriate ferrous ion content.

During the pullulanase production stage, the culture medium should be maintained at a pH between about 6.0 to about 8. Slightly above pH 8.0 pullulanase production by the mutants is terminated. At a pH below 7.2 the production of pullulanase is inhibited. During the initial stages of production the pH generally remains relatively constant. Later in the incubation stage, the pH will tend to significantly increase at a rapid rate. In order to maintain the production culture medium at its optimum elaboration pH, buffering agents or a neutralizing acid in an amount sufficient to maintain the pH at a level between about 7.5 to less than about 8.0 should be utilized, especially during the latter part of incubation. Conventional neutralizing acids such as sulfuric, citric, hydrochloric, lactic, nitric, carbonic, acetic, phosphoric acids, etc. may be used to control and maintain the pH at the appropriate level.

The mutants will propagate over a relatively broad temperature range without an appreciable difference in growth rate. During the initial stages of the pullulanase production the production culture media will normally contain no more than trace amounts of pullulanase. Above 20°C. to about 40°C., the mutants will propagate at approximately an equivalent rate. Optimum pullulanase production by the mutants is more temperature dependent than its growth temperature, with the optimum pullulanase production temperature being within a significantly narrower range. At temperatures below 25°C. or greater than 35°C., pullulanase elaboration is impaired. Due to this temperature dependency, it is advantageous (at least during the latter stages of the production stage) to maintain the culture temperature within this narrow temperature range. Optimum pullulanase yields are achieved when the production culture medium is maintained at about 28°C. Preferably the production culture medium is maintained at its optimum pullulanase elaboration temperatures throughout its propagation and pullulanase production stages.

A particular advantage of this process is the ability to achieve high pullulanase yields within a short period of time. A typical pullulanase process employing different *Aerobacter aerogenes* strains (e.g., ATCC 15050 and ATCC 8724) normally requires more than 35 hours to achieve optimum yields. In the present process, optimum pullulanase yields (in excess of 750 units/ml.) can easily be achieved in a substantially shorter period of time. The entire production cycle commencing with the inoculation thereof with Klebsiella seed culture until its completion can be shortened to from 20 to about 25 hours.

Other production culture media nutrients, minerals, salts and other fermentation aids (such as conventionally employed in other pullulanase production processes) may be utilized, if desired in the present process. Like other pullulanase producing organisms, the Klebsiella organisms herein require nascent oxygen for pullulanase production. Conventional fermentation, agitation and aeration means to provide nascent oxygen with similar aerobic type of organisms may be used for this purpose.

Upon completion of the pullulanase production fermentation, the pullulanase can be recovered by a variety of means. Since the Klebsiella organisms herein provide a production beer of a high yield with a high percentage of indigenous extracellular pullulanase and very loosely bound pullulanase, a nominal amount of additional processing thereof is required to place the pullulanase in a commercially usable form.

Pullulanase yields in excess of 85% of the total pullulanase production can easily be recovered by surfactant treatment of the production culture media. The initial surfactant treatment will place most of the superficially bound enzyme in a water soluble form which can easily be recovered therefrom along with the indigenous extracellular pullulanase. The surfactant-liberated pullulanase along with the indigenous extracellular enzyme may then be concentrated under conditions which do not substantially affect its activity (e.g., vacuum drying at relatively low temperature, ultrafiltration, etc.) and used commercially. Liquid pullulanase concentrates having a pullulanase potency of more than 2,000 units/ml (preferably more than about 3,000 units), can easily be prepared in this manner with the production ferment serving as its liquid carrier. If desired, the fermentation cell debris and insolubles may be separated from the fermentation broth. Alternatively, the production media can be treated with surfactant to liberate the superficially bound enzyme, followed by partitioning of the liquid phase from the insolubles and then precipitation of the pullulanase from the liquid phase via conventional additives therefore and subsequent drying thereof to provide a dry pullulanase preparation. If more complete recovery of pullulanase is desired, the cellular residue can be repeatedly treated with surfactants or alternatively subjected to conditions whereby cellular lysis thereof occurs. It is economically advantageous, however, to recover the pullulanase without lysis of the cells since little, if any, intracellular pullulanase is produced by these Klebsiella organisms.

The superficially bound enzyme is readily placed in a water soluble form by conventional additives and techniques employed for liberating loosely bound enzyme from pullulanase producing organisms. In a commercial operation, it is advantageous to liberate the superficially bound pullulanase without effectuating cellular destrusion or lysis thereof which create additional refining problems and costs. Conventional surface active agents (e.g., sodium lauryl sulfate and Triton X-100[4]) in an amount sufficient to effectively liberate the superficially bound enzyme without causing substantial cellular lysis thereof, can be conveniently used for this purpose. A conventional, pullulanase-liberating non-ionic surfactant in an amount sufficient to provide a production culture media containing between about 0.1% to 0.5% by volume, under agitation for about 5 to about 20 hours, is generally suitable for liberating the superficially bound enzyme. Prolonged surfactant treatment at the more elevated concentrations can cause lysis thereof (e.g., .5% for 25 hours or more).

[4] – an alkyl phenoxy polyethoxy ethanol sold under the trademark of Triton X-100 by Rohm & Haas)

The following examples are merely illustrative and should not be construed as limiting the scope of the invention.

EXAMPLE I

A production culture yielding 790 units of pullulanase for each ml. of culture media broth was prepared by employing *Klebsiella pneumoniae* NRRL-B-5780 as a pullulanase producing organism.

The inoculum nutrient medium consists of (on a weight basis) 2.0% waxy maize starch[5], 2.0% Bacto-Peptone[6], 0.5% ammonium acetate, 0.05% sodium citrate ($Na_3C_6H_5O_7 \cdot 2H_2O$), 0.1% $K_2HPO_4$, 0.1% $KH_2PO_4$, 0.05% $MgSO_4 \cdot 7H_2O$, 0.05% KCl, 0.001% $FeSO_4 \cdot 6H_2O$ and water was prepared. This media was formulated by adding, in sequence, the sodium citrate, the other minerals salts, the peptone and then the waxy maize starch. The resultant mixture was then heated on a steam bath under agitation to provide a homogeneous culture media with the waxy maize starch being thoroughly pasted therein. To each of five 500 ml. bottom baffled DeLong flasks, 100 ml. of the inoculum media and one drop of an antifoam agent (Hodag M-8) was added. The inoculum media was then sterilized at 121°C. for 15 minutes. The flasks containing the nutrient media were then inoculated with *Klebsiella pneumoniae* NRRL-B-5780 (agar slants). The flasks were then incubated for 16 hours at 28°C. at 265 rpm on a New Brunswick rotary shaker and the resultant inoculum was utilized as seed inoculum for the production culture media.

[5] — STA-TAPE 110 — manufactured by the A. E. Staley Manufacturing Company - An intermediate viscosity, acid thinned, granular waxy maize starch (100% amylopectin) typically having a Brookfield viscosity of about 2000 cps (Number 3 spindle, 20 rpm, at 150°F. at a dry solids of 40–45%) and a D.E. of less than 1%.

[6] — A peptone preparation of Difco Labs., Detroit, Michigan.

A pullulanase production nutrient media was prepared by dissolving 60 parts by weight of sodium citrate ($Na_3C_6H_5O_7 \cdot 2H_2O$) in 1000 parts (1 liter) by weight tap water (20°C.). Three hundred and fifty parts by weight of corn steep liquor (d.s.b.) was slowly added to the sodium citrate solution (with stirring) to provide a sodium citrate-corn steep liquor solution thereof. The resultant solution was adjusted to pH 6.3 by the addition of 50% solution of potassium hydroxide.

A pasted waxy maize preparation was then separately prepared by slowly adding, with agitation, three hundred and fifty parts by weight of the low viscosity waxy maize starch[7] to 5000 parts by weight (5 l.) water and heating to 96°C. After thoroughly pasting the waxy maize starch, fifty parts by weight potassium chloride and 70 parts by weight ammonium sulfate were added to provide an aqueous media thereof.

[7] — See footnote 5 above

The sodium citrate-corn steep liquor solution and the above aqueous starch paste media (at 96°C.) were then admixed together with additional hot tap water to provide a ten liter aqueous production culture media. This ten liter aqueous production media was then placed in a fermentor (14 liter capacity New Brunswick MF 114 Fermentor) and autoclaved at 121°C. for 45 minutes.

A sterile (autoclaved at 121°C. for 15 minutes) 0.036 molar acidified, ferrous sulfate solution dissolved in 0.08M hydrochloric acid solution was prepared to provide supplemental ferrous ion. Immediately prior to inoculating the fermentation media with the seed inoculum, 20 ml. of the ferrous sulfite solution was dissolved in the fermentor to provide a production nutrient media containing 4.0 milligrams of ferrous ion (20 mg of ferrous sulfate) per liter of aqueous production media.

The above aqueous production media was then inoculated with the seed inoculum (initial pH 6.3). The inoculated aqueous production media was incubated at 28°C., a stirrer speed of 550 rpm and aeration rate of 6 v.v.m. (volume air per volume fermentation broth per minute) for 23 hours. Foam development (only a problem at the very beginning of the fermentation) was suppressed by automatic addition of a defoaming agent (Hodag M-8 antifoam). During the initial 9 hours of fermentation, the pH gradually increased to 7.75. Thereafter the pH was maintained throughout the production cycle at 7.75 by means of an automatic sensing and metering device, whereby it was neutralized with 14M aqueous acetic acid solution (80% acetic acid).

After fermenting for 23 hours the optimum pullulanase yields (790 units of pullulanase per milliliter of fermentation broth) had been achieved.

In determining the yields of extracellular pullulanase, superficially bound pullulanase and intercellular pullulanase, the following pullulanase assay procedure was used.

The pullulanase assay method is a modification of the dinitrosalicylic acid (DNSA) procedure of Fisher, E. H. and Stein, E. A., (1958), J. Biol. Chem. 232:867–879 as immediately defined hereinafter.

REAGENTS

DNSA Reagent — 3,5-dinitrosalicylic acid reagent was freshly prepared as described by Fisher and Stein (1958):

1. Add 20.0G DNSA in 400 mls of distilled water.
2. Add dropwise to 1 above, while stirring, a NaOH solution (32.0g sodium hydroxide (d.s.b.) in 300 mls distilled water. This solution should be clear; if not, heat gently until clear.
3. Gradually and incrementally add 600.0g of potassium sodium tartrate to 2 above.
4. Add distilled water to a final volume of 2.0 liters.
5. Filter the solution through a large sintered glass filter.

ACETATE BUFFER — 0.1M, — pH 5.0 acetate buffer (sodium acetate and acetic acid)

SUBSTRATE — 1.0% (by weight) aqueous pullulanase solution.

PROCEDURE

A 0.5 ml portion of a pullulanase test sample is added at timed intervals to 4.5 mls of temperature equilibrated pullulan substrate (2.0 ml of 0.1M. — pH 5.0 acetate buffer and 2.5 ml of pullulan solution) in 18 × 150 mm test tubes. After 0, 6 and 12 minute incubation, 1.0 ml of the digestion mixture is added to 1.0 ml of DNSA reagent (with thorough mixing) to stop the digestion reaction. Color is then developed by heating the tubes for 5.0 minutes in a 100°C. water bath. Immediately after heating, the tubes are cooled 5 minutes in cold water 17°C.). After cooling, 10.0 ml of distilled water (20°C.) is added thereto and each tube is mixed thoroughly.

The amount of color developed is determined with a Bausch and Lomb Spectronic 70 spectrophotometer as the percent transmittance at 545 nm ($\%T_{545}$) against a reagent blank set for 100%T. Percent transmittance readings are converted to absorbance according to the formula $$A_{545} = 2 - \log \%T_{545}$$

The change in absorbance per unit time ($A_{545}$) is expressed as (mg maltose equivalent) from a standard calibrated maltose curve.

DEFINITION OF A PULLULANASE UNIT

One unit of pullulanase is defined as that amount of enzyme which will produce 1 mg of maltose equivalent per ml of digest from a 0.5% pullulan solution in 60 minutes at 45°C. and pH 5.0. Based upon the pullulanase assay procedure, the units of pullulanase per ml of production culture media may be determined by the following equation:

$$\text{units/ml} = \frac{\text{mg of maltose}}{1 \text{ ml of digest}} \times \frac{60 \text{ min.}}{\text{digestion time of test sample (in min.)}} \times \frac{1 \text{ ml}}{.5 \text{ ml (diluted test sample)}}$$
$$\times \frac{\text{final volume in dilution blank}}{\text{mls added to dilution blank}}$$

In determining the amount of extracellular pullulanase in the production culture media, a 5 ml. uniform pullulanase test sample (homogeneous mixture of insolubles and solubles of ferment) was withdrawn from the fermentor. This sample was taken while the fermentor was operatively engaged. The test sample was centrifuged at a centrifugal force of 7,500 $x_g$ for 5 minutes. The resultant supernatant containing the extracellular pullulanase was carefully separated by decantation from the centrifuged insolubles. Pursuant to this pullulanase assay method mentioned above, the production culture media had an extracellular pullulanase assay of 390 units/ml of production broth. While the agitator of the fermentor was engaged (550 rpm) 40 milliliters of a non-ionic surfactant (Triton X-100[8]) was added to the fermentor. The non-ionic surfactant and culture beer (production culture media) was continuously agitated in the fermentor (at 550 rpm) for 12 hours, to convert the loosely bound pullulanase to a water-soluble form. The culture beer containing the water-soluble pullulanase was then centrifuged and separated under the same assay procedure as employed in obtaining the test sample of extracellular pullulanase. The resultant supernatant was found to contain 720 units of pullulanase for each ml of production culture media (includes both extracellular and surfactant solubilized pullulanase).

8 — See Footnote 4 above.

In order to determine the total pullulanase produced by the NRRL-B-5780 mutant herein, an exhaustive pullulanase extraction without lysis of the cells was conducted. The procedure employed in the exhaustive extraction of the pullulanase from the production ferment was as follows:

1. One hundred milliliters of fermented beer was placed in 500 ml. Erlenmeyer flask and 0.5 mls of surfactant (Triton X-100) was added thereto.
2. The flask was then agitated for 20 hours in a rotary shaker (New Brunswick Rotary Shaker at 265 rpm and 28°C.).
3. Pullulanase test samples were then withdrawn with the pullulanase assay thereof being made by the above mentioned pullulanase assay test procedure.
4. The insolubles were separated from liquor via centrifuging (as mentioned hereinbefore) and decantation.
5. The insoluble centrifuged residue was washed twice with 100 ml. of distilled water with the pullulanase assay being conducted upon the resultant wash water.
6. The washed, centrifuged solids were then placed into a 500 ml. Erlenmeyer flask which contained .4 grams of the surfactant and 100 ml. of distilled water.
7. Steps 2–6 were sequentially repeated until the pullulanase assay in step 3 indicated a pullulanase yield of less than 0.5 pullulanase units/ml.

The initial assay for pullulanase in step 3 on the fermented beer substantially corresponded in value to the 720 units/ml mentioned above. A major portion of the total pullulanase assayed thereafter was obtained immediately on the next surfactant-extraction cycle (i.e., step 6 followed by steps 2 and 3). Thereafter, subsequent pullulanase assays of step 3 showed significantly lesser pullulanase unit value. The total amount of pullulanase units assayed by the exhaustive pullulanase extraction was 70 units/ml of fermented beer. Thus, the total pullulanase yield of both extracellular pullulanase and superficially bound pullulanase was 790 units/ml of production culture media. Because of the high recoverable yields initially obtained by a single surfactant extraction step (i.e., 720 units/ml), the subsequent solubilization and treatment of cell debris with surfactant is most suitably eliminated in a commercial operation. The ratio of extracellular pullulanase to superficially bound pullulanase was 39:40.

Upon completion of the aforementioned exhaustive pullulanase extraction, the insoluble cellular residue (from step 5) was subjected to sonification to effectuate lysis thereof. The resultant cell free lysate was assayed for pullulanase and found to contain none.

This example was repeated employing *Klebsiella pneumoniae* NRRL-B-5783 in one production run and *Klebsiella pneumoniae* NRRL-B-5784 in another production run. The NRRL-B-5783 strain yielded 690 units/ml. and NRRL-B-5784 yielded 744 units/ml pursuant to the above assay procedure. The production culture beer assay indicated these two Klebsiella strains produced pullulanase in substantially the same form as did the NRRL-B-5780 strain. Neither strain produced a measurable amount of intracellular enzyme. As with NRRL-B-5780, the pullulanase produced by the organism was essentially in the extracellular and superficially bound form in substantially the same proportions as the NRRL-B-5780 strain.

EXAMPLE II

This example illustrates the effect which divergent carbohydrate source materials have upon pullulanase elaboration. The culture media was the same as the inoculation media in Example I, except for carbohydrate source materials as designated in Table I. The Runs were incubated for 36 hours. For comparative purposes and under equivalent incubation conditions, *Aerobacter aerogenes* 15050 was used in each Run. The results are tabulated in Table I.

NRRL-B-5780. Conversely, pullulanase production with *Aerobacter aerogenes* ATCC 15050 (e.g., see Runs 6, 7, 8, 9 and 10) was significantly enhanced in the presence of maltose. The highest pullulanase yield for *Aerobacter aerogenes* ATCC 15050 (Run 6) was achieved with maltose alone, but this yield was only 17.6% of NRRL-B-5780 in Run 1. In contrast, NRRL-B-5780 only yielded its 11.9% of Run 1 counterpart when 2% maltose was employed as a sole carbohydrate source. Pullulan as a sole carbohydrate source had a similar suppressing effect upon *Klebsiella pneumoniae* NRRL-B-5780 whereas pullulanase production with *Aerobacter aerogenes* ATCC 15050 was enhanced thereby (see Run 3). In general, *Aerobacter aerogenes* ATCC 15050 was incapable of effectively elaborating pullulanase when starch or starch hydrolyzates having a relatively high degree of polymerization were employed as the major carbohydrate source (e.g., see Runs 1–3, 5, 9, 10 and 15). In comparison, the mutant herein has a significantly greater capacity to produce pullulanase in the presence of pasted starches and especially a production culture media which contains a high amylopectin concentration. As evidenced in Run 11, *Aerobacter aerogenes* ATCC 15050 was incapable of elaborating pullulanase when dextrose was employed as a sole carbohydrate source whereas *Klebsiella pneumoniae* can produce a small amount of pullulanase under the production conditions of this example.

TABLE I

| Run No. | PRODUCTION CULTURE MEDIA CARBOHYDRATE % by weight based on total culture media weight | AEROBACTER AEROGENES ATCC 15050 % extracellular pullulanase | % Yield | KLEBSIELLA PNEUMONIAE NRRL-B-5780 % extracellular pullulanase | % Yield |
|---|---|---|---|---|---|
| 1 | 2% intermediate viscosity waxy maize[9] | 20% | 2.5% | 52% | 100% |
| 2 | 2% low viscosity waxy maize[10] | 22% | 2.5% | 50% | 86% |
| 3 | 2% pasted Pearl starch[11] | 20% | 2.2% | 48% | 67% |
| 4 | 2% pullulan | 33% | 13.2% | 47% | 11.9% |
| 5 | 2% waxy starch[12] | 20% | 3.8% | 49% | 85.5% |
| 6 | 2% maltose | 35% | 17.6% | 51% | 12.6% |
| 7 | 1.5% maltose + .5% intermediate viscosity waxy maize[9] | 30% | 11.3% | 50% | 15.1% |
| 8 | 1% maltose + 1% intermediate viscosity waxy maize[9] | 30% | 10.7% | 50% | 15.7% |
| 9 | 0.5% maltose + 1.5% intermediate viscosity waxy maize[9] | 20% | 3.8% | 51% | 25.2% |
| 10 | 0.25% maltose + 1.75% intermediate viscosity waxy maize[9] | 21% | 3.1% | 48% | 55.3% |
| 11 | 2% dextrose | 0% | 0.0% | 30% | 3.1% |
| 12 | 2% lactose | 23% | 2.5% | 51% | 18.2% |
| 13 | 1% lactose + 1% intermediate viscosity waxy maize[9] | 21% | 2.5% | 53% | 18.2% |
| 14 | 2% amylose | 0% | 0.0% | 0% | 0.0% |
| 15 | 2% maltodextrin[13] | 19% | 6.0% | 47% | 24.5% |
| 16 | 2% 12 D.E. corn starch[14] | 14% | 4.4% | 47% | 61.6% |
| 17 | No carbohydrate present | 0% | 0.0% | 0% | 0.0% |

[9]See Footnote 5 above.
[10]STA-TAPE 100 — manufactured by the A. E. Staley Manufacturing Company — A low viscosity, acid thinned, granular waxy maize starch (100% amylopectin) typically characterized as having a Brookfield viscosity of about 500 cps (No. 2 spindle, 20 rpm, 150°F. at a dry solids of 40–45%) and a D.E. of less than 1%.
[11]Unhydrolyzed, pasted pearl starch.
[12]Unhydrolyzed, pasted waxy maize starch.
[13]Saccharide distribution: $D.P._1 — 3.1\%$; $D.P._2 — 5.65\%$; $D.P._3 — 7.38\%$; $D.P._4 — 5.14\%$; $D.P._5 — 4.86\%$; $D.P._6 — 9.81\%$; $D.P._{7\ and\ 8} — 13.82\%$; $D.P._9 — 3.09\%$; $D.P._{10+} — 47.15\%$.
[14]Saccharide distribution (D.P. — %): 1 — .6%; 2 — 3.3%; 3 — 6.1%; 4 — 4.0%; 5 — 4.5%; 6 — 6.4%; 7 — 5.7%; 8 — 4.0%; 9 — 3.0%; 10 — 2.6%; $DP_{11–30} — 18.2\%$; $D.P._{30+} — 41.56\%$.

In Run 1 of Table 1, the reported results for *Klebsiella pneumoniae* NRRL-B-5780 are correlated to those of Example I. For comparative purposes the tabulated percentage yields are relative to those of NRRL-B-5780 in Run 1. As illustrated by Runs 6, 7, 8, 9 and 10, increased concentration of maltose in the production culture media inhibits the pullulanase production with With the exception of Run 11, (i.e., dextrose as sole carbohydrate) *Klebsiella pneumoniae* NRRL-B-5780 elaborated between about 47% to about 53% extracellular pullulanase (remaining portion thereof being essentially in superficially bound form) whereas the *Aero-*

*bacter aerogenes* ATCC 15050 produced in each of the Runs 35% or less extracellular pullulanase.

As previously mentioned, pullulanase producing organisms of the *Aerobacter aerogenes* type generally require a carbohydrate inducer to effectuate optimum pullulanase yields. The mutants of this invention are suppressed by these carbohydrate inducers.

A starch substrate having a low D. E. and high amylopectin content enhances the pullulanase production with NRRL-B-5780. This is shown by the NRRL-B-5780 Runs 1, 2 and 5 yields. The viscosity characteristics of these amylopectin (at 40–45% paste level) are about 5000 cps, 2000 cps and an extremely high viscosity characteristics. As evident from Runs 3 and 8, culture media substrates of a higher amylopectin content are more conducive to pullulanase production than the pasted pearl starch. In Runs 15 and 16 the amylopectin portion of starch is excessively hydrolyzed and also contain carbohydrate source materials of a relatively high percentage of low D.P. saccharides which inhibited its pullulanase production capacity.

EXAMPLE III

Enhanced pullulanase yields are achieved when the production culture media contains supplemental ferrous ions. Except for different levels of ferrous ion, corn steep liquor and incubation time, as indicated in Table II, pullulanase production under this example was the same as Example I. The results are tabulated in Table II.

TABLE II

| Run No. | (D.S.B.) % corn steep | MgFe++ mg/liter | Yield (Units/ml of culture media) | Time (Hrs) |
|---|---|---|---|---|
| 18 | 4.0% | 3.0 | 744 u/ml | 28.0 |
| 19 | 3.5% | 4.0 | 790 u/ml | 26.0 |
| 20 | 3.0% | 4.4 | 730 u/ml | 27.0 |
| 21 | 3.0% | 0.0 | 656 u/ml | 28.0 |
| 22 | 3.5% | 4.4 | 780 u/ml | 27.5 |
| 23 | 3.5% | 6.4 | 775 u/ml | 27.5 |

As evident by comparing Runs 20 and 21 above, the employment of supplemental ferrous ions (corn steep employed herein contained 0.7 mg. of ferrous ion) per liter, provided more than a 10% increase in pullulanase yields. On a comparative basis, the 656 units/ml yield for Run 21 still represents a superior yield improvement over those obtained with *Aerobacter aerogenes*. As illustrated by a comparison of the yields in Runs 19, 20, 22 and 23, an increase in ferrous ions above 4.0 mg/liter provided higher yields than those achieved without supplemental ferrous ions, but did not enhance yields above that of Run 19.

The organisms employed in this invention are characterized as elaborating more pullulanase units when amylopectin is employed as a sole carbohydrate comparative to pullulanase elaboration when a carbohydrate selected from the group consisting of maltose, dextrose, lactose and pullulan is employed as the sole carbohydrate source. In determining the comparative pullulanase yields with these divergent carbohydrates as a sole carbohydrate source, the production culture media under the production incubation conditions as specified in Example I should be employed except for the substitution therein of sole carbohydrate source material. The ability to elaborate pullulanase in the presence of dextrose as a sole carbohydrate source is likewise determined in accordance with the Example I media and production culture. The pullulanase units/ml of production culture media herein are determined in accordance with the pullulanase assay procedure of Example I. The amount of extracellular pullulanase is ascertained upon the basis of the amount of water soluble pullulanase in the production media prior to release of loosely bound pullulanase therefrom (e.g., prior to surfactant liberation thereof) as indicated in Example I. The superficially bound pullulanase is ascertained via the pullulanase assay via the surfactant extraction thereof (including the units/ml of production media by exhaustive surfactant extraction without lysis) of Example I. The ratio of extracellular pullulanase to superficially bound pullulanase (on a unit/ml of production beer) also is determined pursuant to the assay procedure of Example I.

Since many embodiments of this invention may be made and since many changes may be made in the embodiments described, the foregoing is interpreted as illustrative and the invention is defined by the claims appended hereafter.

What is claimed is:

1. In a method for producing pullulanase by inoculating an aqueous nutrient medium containing assimilable carbon and assimilable nitrogen sources with an aerobic, pullulanase producing microbial organism to provide a culture thereof, incubating the culture under aerobic conditions conducive to the production of pullulanase and thereby providing production culture media thereof, and thereafter recovering a pullulanase preparation from the production culture media, the improvement which comprises:
   A. inoculating a nutrient medium with a pullulanase producing organism derived from the Klebsiella genus, wherein said organism is characterized as:
      a. elaborating at least three times more pullulanase when amylopectin of a D.E. of less than 2.0 is employed as the sole carbohydrate source comparative to pullulanase elaboration in a nutrient medium wherein the major carbohydrate (on an equivalent carbohydrate weight basis) is a carbohydrate source member selected from the group consisting of maltose, dextrose, lactose and pullulan;
      b. elaborating pullulanase at a ratio of extracellular pullulanase to superficially bound cell pullulanase between about 2:3 to less than 7:3 when said organism is elaborated in a nutrient medium containing amylopectin as the sole carbohydrate source;
      c. elaborating pullulanase in a nutrient medium which contains dextrose as a sole carbohydrate source; and
   B. incubating the pullulanase producing organism in a nutrient medium for a period of time sufficient to provide a production culture media which contains at least 350 units of pullulanase for each milliliter of production culture media with the production culture media containing a ratio of extracellular pullulanase to superficially bound pullulanase between about 2:3 to less than about 7:3.

2. The method according to claim 1 wherein the nutrient medium contains amylopectin as the major carbohydrate source (on a total carbohydrate weight basis) and the nutrient medium contains a weight ratio (d.s.b.) of amylopectin to a carbohydrate member selected from the group consisting of pullulan, maltose, dextrose and lactose of at least 3:1.

3. The method according to claim 2 wherein the carbohydrate source material in the nutrient medium consists essentially of an amylopectin of a D. E. of less than 2.0% and the incubation of the nutrient medium is conducted at a temperature of 25°C. to less than 35°C. for a period of time sufficient to provide a pullulanase yield of at least 500 pullulanase units per ml. of production culture media.

4. The method according to claim 3 wherein the pullulanase producing organism is at least one member selected from the group consisting of Klebsiella pneumoniae NRRL-B-5780, Klebsiella pneumoniae NRRL-B-5783 and Klebsiella pneumoniae NRRL-B-5784.

5. The method according to claim 1 wherein the nutrient medium is characterized as being essentially free from fermentable sugars and pullulan and contains amylopectin as a major carbohydrate source material.

6. The method according to claim 5 wherein the assimilable carbohydrate source of the nutrient media consists essentially of an assimilable starch having a D.E. of less than about 5%.

7. The method according to claim 5 wherein the nutrient media carbohydrate source material consists essentially of amylopectin and the incubation of the inoculated nutrient media is continued for a period of time sufficient to provide at least 700 pullulanase units for each milliliter of production culture media.

8. The method according to claim 7 wherein the organism is characterized as elaborating in the presence of amylopectin as a sole carbohydrate source, a ratio of extracellular pullulanase units to superficially bound pullulanase units between about 3:4 to about 2:1.

9. The method according to claim 8 wherein the nutrient medium contains (on a 100 parts by weight culture media basis) from about 0.25 to about 2 parts by weight of an assimilable ammonium salt and about 3 to about 4 parts by weight corn steep liquor.

10. The method according to claim 1 wherein the carbohydrate source of the nutrient medium consists essentially of an assimilable starch having a D.E. of less than 20%.

11. The method according to claim 10 wherein the nutrient media contains an assimilable inorganic nitrogen source in an amount sufficient to increase pullulanase elaboration by the organisms.

12. The method according to claim 11 wherein the weight ratio (dry weight basis) of amylopectin to non-amylopectin carbohydrates in the nutrient medium is at least 9:1.

13. The method according to claim 12 wherein the incubation of the inoculated nutrient medium is conducted for a period of time sufficient to provide a production culture media containing more than about 690 pullulanase units of pullulanase for each milliliter of production culture media.

14. The method according to claim 13 wherein prior to recovery of the pullulanase from the production culture media, the production culture media is treated with an effective amount of a surfactant to convert the superficially bound pullulanase to a water-soluble form and thereby provide a production culture media which contains at least 85% of the total pullulanase yield in a water-soluble form.

15. The method according to claim 14 wherein the carbohydrate source consists essentially of amylopectin.

16. The method according to claim 10 wherein substantially all of the pullulanase produced by the organism is in the extracellular and superficially bound form with the unit ratio of extracellular pullulanase to superficially bound pullulanase being between about 3:4 to about 2:1.

17. The method according to claim 16 wherein the production of pullulanase is conducted at a temperature greater than 25°C. to less than 35°C.

18. The method according to claim 17 wherein the nutrient media is inoculated and incubated with at least one organism selected from the group consisting of Klebsiella pneumoniae NRRL B-5780, Klebsiella pneumoniae NRRL B-5783, Klebsiella pneumoniae NRRL B-5784 and mutants thereof.

19. The method according to claim 18 wherein the nutrient media contains more than 1 mg of ferrous ion for each liter of nutrient medium.

20. The method according to claim 19 wherein the carbohydrate source material consists essentially of amylopectin having a D.E. of less than 2%.

21. The method according to claim 1 wherein the nutrient media comprises (on a 100 parts by weight nutrient medium basis) from about 1 to about 6 parts by weight amylopectin (d.s.b.) from about 2 to about 15 parts by weight nitrogen source (d.s.b.) with said nitrogen source being comprised of assimilable organic nitrogen source and assimilable inorganic nitrogen source respectively at a weight ratio (d.s.b.) ranging from about 1:1 to about 15:1, and an effective amount of ferrous ion which in combination with the assimilable amylopectin and the assimilable nitrogen source provides a nutrient medium to enable the organism to elaborate at least 500 units of pullulanase per milliliter of nutrient medium with the incubation of said nutrient medium being conducted at a temperature of 25°C to 35°C. for a period of time sufficient to provide a production culture media of at least 500 pullulanase units per ml. of production culture media.

22. The method according to claim 21 wherein the nutrient medium contains (on a 100 parts by weight of nutrient) from about 3 to about 5 parts by weight (d.s.b.) corn steep liquor, about 0.25 to about 2 parts by weight of an assimilable water-soluble inorganic nitrogen salt, and about 2 mg to about 5 mg of ferrous ion for each liter of nutrient medium.

23. The method according to claim 22 wherein the organism is a *Klebsiella pneumoniae*.

24. The method according to claim 23 wherein the assimilable water-soluble inorganic salt consists essentially of an assimilable ammonium salt.

25. The method according to claim 1 wherein the organism is *Klebsiella pneumoniae* NRRL-B-5780.

26. A pullulanase preparation suitable for use in hydrolyzing alpha-1,6-glucosidic starch linkages and prepared from a culture media containing at least 500 units of pullulanase for each milliliter of culture media with a ratio of extracellular pullulanase to superficially bound pullulanase from about 3:4 to about 2:1 wherein said preparation is elaborated by a Klebsiella pneumoniae organism characterized as:

a. elaborating at least three times more pullulanase when amylopectin of a D.E. of less than 2.0 is employed as the sole carbohydrate source comparative to pullulanase elaboration in a nutrient medium wherein the major carbohydrate (on an eqivalent carbohydrate weight basis) is a carbohydrate source member selected from the group consisting of maltose, dextrose, lactose and pullulan;

b. elaborating pullulanase at a ratio of extracellular pullulanase to superficially bound cell pullulanase between about 2:3 to less than about 7:3 when said mutant is elaborated in a nutrient medium containing amylopectin as the sole carbohydrate source; and c. elaborating pullulanase in a nutrient medium which contains dextrose as a sole carbohydrate source.

27. The preparation according to claim 26 wherein the organism is at least one member selected from the group consisting of *Klebsiella pneumoniae* NRRL-B-5780, *Klebsiella pneumoniae* NRRL-B-5783 and *Klebsiella pneumoniae* NRRL-B-5784.

28. The preparation according to claim 27 wherein the organism is *Klebsiella pneumoniae* NRRL-B-5780.

29. In a method of hydrolyzing the alpha-1,6-glucosidic linkages of a starch to a starch hydrolyzate with a pullulanase preparation, the improvement which comprises conducting the hydrolysis in the presence of a pullulanase preparation derived from Klebsiella organisms characterized as:

a. elaborating at least three times more pullulanase when amylopectin of a D.E. of less than 2.0 is employed as the sole carbohydrate source comparative to pullulanase elaboration in a nutrient medium wherein the major carbohydrate (on an equivalent carbohydrate weight basis) is a carbohydrate source member selected from the group consisting of maltose, dextrose, lactose and pullulan;

b. elaborating pullulanase at a ratio of extracellular pullulanase to superficially bound cell pullulanase between about 2:3 to less than about 7:3 when said mutant is elaborated in a nutrient medium containing amylopectin as the sole carbohydrate source; and c. elaborating pullulanase in a nutrient medium which contains dextrose as a sole carbohydrate source.

30. The method according to claim 29 wherein the organism is at least one member selected from the group consisting of *Klebsiella pneumoniae* NRRL-B-5780, *Klebsiella pneumoniae* NRRL-B-5783, *Klebsiella pneumoniae* NRRL-B-5784 and mutants thereof.

31. The method according to claim 29 wherein the hydrolysis is conducted in combination with another amylase to hydrolyze the starch to a conversion syrup product.

32. The method according to claim 31 wherein the pullulanase preparation is produced by *Klebsiella pneumoniae* NRRL-B-5780 or a mutant thereof.

* * * * *

UNITED STATES PATENT AND TRADEMARK OFFICE
CERTIFICATE OF CORRECTION

PATENT NO. : 3,963,575
DATED : June 15, 1976
INVENTOR(S) : Anthony A. Bulich

It is certified that error appears in the above-identified patent and that said Letters Patent are hereby corrected as shown below:

Column 1, line 24, for "conductive" read ---conducive---
Column 1, line 54, for "excess" read ---excessive---
Column 1, line 57, for "on" read ---to---
Column 4, bridging lines 36/37, for "is definitely affected" read ---is affected---
Column 4, line 57, for "above" read ---about---
Column 5, line 13, for "bound elaborated" read ---bound pullulanase elaborated---
Column 5, line 22, for "of pullulanase tightly cell-bound (e.g." read ---of tightly cell-bound pullulanase (e.g.---
Column 5, line 52, for "mucilaginous polysaccharide will adversely" read ---mucilaginous polysaccharides adversely---
Column 9, line 27, for "provide" read ---provides---
Column 10, line 31, for "to from 20" to read ---to 20---
Column 11, line 21, for "destrusion" read ---destruction---
Column 11, line 30, for "volume, under" read ---volume surfactant, under---
Column 12, bridging lines 11/12, for "by the addition of 50%" read ---by addition of a 50%---
Column 12, line 42, for "28°C. a stirrer speed of 550 rpm and aeration" read ---28°C. with the fermentor being operated at a stirrer speed of 550 rpm and an aeration---
Column 13, line 1, for "G" read ---g---
Column 16, line 8, for "yielded its 11.9% of Run" read ---yielded 12.6% of the Run---
Column 17, line 14, for "Runs 3 and 8" read ---Runs 1 and 3---
Column 17, Table 2 heading column 3, for "MgFe$^{++}$" read ---Fe$^{++}$---
Column 22, line 9, for "mutant" read ---organism---

Signed and Sealed this

Nineteenth Day of April 1977

[SEAL]

Attest:

RUTH C. MASON
Attesting Officer

C. MARSHALL DANN
Commissioner of Patents and Trademarks